US008088950B2

(12) United States Patent
Bock et al.

(10) Patent No.: US 8,088,950 B2
(45) Date of Patent: Jan. 3, 2012

(54) PROCESS FOR THE PREPARATION OF TRIAMIDES FROM AMMONIA AND AMIDO-DICHLORIDES

(75) Inventors: Michael Bock, Ruppertsberg (DE); Oliver Huttenloch, Ispringen (DE); Patrick Deck, Mannheim (DE); Oliver Bey, Niederkirchen (DE); Heiner Schelling, Kirchheim (DE); Markus Siegert, Heidelberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/935,934

(22) PCT Filed: Mar. 26, 2009

(86) PCT No.: PCT/EP2009/053577
§ 371 (c)(1),
(2), (4) Date: Oct. 1, 2010

(87) PCT Pub. No.: WO2009/121786
PCT Pub. Date: Oct. 8, 2009

(65) Prior Publication Data
US 2011/0028761 A1 Feb. 3, 2011

(30) Foreign Application Priority Data

Feb. 4, 2008 (EP) ..................................... 08153960

(51) Int. Cl.
*C07F 9/06* (2006.01)
(52) U.S. Cl. .......................................................... 564/14
(58) Field of Classification Search ..................... 564/14
See application file for complete search history.

(56) References Cited

U.S. PATENT DOCUMENTS

| 5,770,771 A | 6/1998 | Sulzer et al. |
| 5,883,297 A * | 3/1999 | Sulzer et al. ..................... 564/14 |
| 2008/0287709 A1 | 11/2008 | Huttenloch et al. |
| 2010/0168256 A1 | 7/2010 | Rittig et al. |
| 2010/0215611 A1 | 8/2010 | Rittig et al. |

FOREIGN PATENT DOCUMENTS

| DE | 102005053541 A1 | 5/2007 |
| WO | WO-98/31691 A1 | 7/1998 |
| WO | WO-2007/054392 A1 | 5/2007 |

OTHER PUBLICATIONS

Trenkel, M.E., "Controlled-release and stabilized fertilizers in agriculture," Improving Fertilizer Use Efficiency, 1997, pp. 29-39, International Fertilizer Industry Association, Paris: France.

* cited by examiner

*Primary Examiner* — Peter O Sullivan
(74) *Attorney, Agent, or Firm* — Connolly Bove Lodge & Hutz LLP

(57) ABSTRACT

The invention relates to a process for the preparation of triamides from ammonia and amido-dichlorides.

10 Claims, No Drawings

PROCESS FOR THE PREPARATION OF TRIAMIDES FROM AMMONIA AND AMIDO-DICHLORIDES

PRIORITY

Priority is claimed as a national stage application, under 35 U.S.C. §371, to PCT/EP2009/053577,filed Mar. 26, 2009, which claims priority to European application 08153960.3, filed Apr. 2, 2008. The disclosures of the aforementioned priority applications are incorporated herein by reference in their entirety.

The invention relates to a process for the preparation of triamides from ammonia and amido-dichlorides.

Preferred embodiments can be found in the description and the claims, and the examples. Combinations of preferred embodiments do not go beyond the scope of the invention.

Thiophosphoric triamides, specifically N-n-butylthiophosphoric triamide (NBPT), are effective urease inhibitors which are employed in urea-based fertilizer compositions. The use of such urease inhibitors can improve the efficacy of urea fertilization since losses caused by the urease-catalyzed degradation of urea in the soil are reduced (Trenkel, M. E., "Controlled-Release and Stabilized Fertilizers in Agriculture", IFA 1997, ISBN: 2-9506299-0-3; p. 30 et seq.).

U.S. Pat. No. 5,770,771 describes a process for the preparation of hydrocarbylthiophosphoric triamides. In this process, ammonium and N-hydrocarbylammoniothiophosphoryl dichloride are mixed in a reaction chamber in a ratio of 16:1, producing a reaction mixture comprising hydrocarbylthiophosphoric triamide, and in which the ammonium chloride co-product formed is kept in solution in the ammonium which has been added in a large excess. The residence time of the reaction mixture in the reactor is from 1 to 10 minutes. The product of interest is separated off by means of distillation.

WO 2007/054392 describes a process for separating acids from reaction mixtures, which process is employed for the preparation of alkylthiophosphoric triamides from ammonia and alkylthiophosphoryl dichloride, an amido-dichloride. Gaseous ammonia is passed through an amido-dichloride solution and reacted. The residence time of the reaction mixture in the reactor is 60 minutes. The product of interest is isolated by means of phase separation, precipitated in the phase by lowering the temperature, and purified via a filtration step.

WO 98/31691 describes a process for the preparation of hydrocarbylthiophosphoric triamides from ammonia and hydrocarbylaminothiophosphoryl dichloride, an amido-dichloride. Here, ammonia is placed into a reactor comprising the amido-dichloride and reacted, the residence time of the reaction mixture in the reactor being 90 minutes. The product of interest is purified in a thin-film evaporator.

It has been found that a prolonged reaction time gives rise to dimeric, oligomeric and polymeric reaction products of the product triamide and the starting material amido-dichloride, which increase the mean molar mass of the reaction mixture and adversely affect the quality of the product of interest.

An increased proportion of the oligomeric co-products makes handling more difficult during the process and raises the production costs. The impurities are difficult to separate from the product of interest by means of distillation, and recrystallization entails considerable outlay in terms of apparatuses and energy.

It was therefore an object of the present invention to provide a process which reduces the formation of oligomeric and polymeric reaction products in the preparation of triamides from ammonia and amido-dichloride.

This object has been achieved by a process for the preparation of triamides from ammonia and amido-dichlorides, wherein the starting materials are mixed with each other, and reacted, in a back-mixing-free manner, wherein the concentration of the amido-dichloride in the mixing device is at all times below 0.2 (mol/mol) % of the reaction mixture based on the volume of the reaction mixture.

In one embodiment of the process according to the invention, the mixing time of the starting materials is less than one second.

In one embodiment of the process according to the invention, the mixing of the starting materials is performed by means of nozzle, rotor-stator mixer, reaction mixing pump or jet mixer equipped with nozzle.

In a further embodiment of the process according to the invention, the mixture is transferred into a tube reactor.

In a further embodiment of the process according to the invention, the tube reactor is a heat exchanger.

In a further embodiment of the process according to the invention, the starting materials are cooled before mixing to such an extent that no substantial reaction occurs in the mixing device.

In a further embodiment of the process according to the invention, the heat of reaction is dissipated by evaporating ammonia.

In a further embodiment, the reaction discharge of the tube reactor is transferred into a column and the triamide is drawn off at the column bottom.

In a further embodiment, the triamide is an N-alkylthiophosphoric triamide.

The preparation of triamides is known per se to a person skilled in the art or is possible by methods known per se to a person skilled in the art. Also, the preparation of the amido-dichloride required for the preparation of triamides is known per se to a person skilled in the art or is possible by methods known per se to a person skilled in the art. The amido-dichloride which is required for the preparation of the triamide according to the invention and which is used as starting material in the process according to the invention can be prepared for example as described in WO2007/054392 from the reaction of trichlorides with at least one primary or secondary amine in a solvent.

An example of a suitable solvent is ethyl acetate. However, all the other known, preferably polar, solvents such as esters and ketones or tetrahydrofuran (THF) are also suitable.

The reaction mixture of this reaction comprises amido-dichlorides and can be employed directly in the process according to the invention for the reaction with ammonia to give triamide. Alternatively, the amido-dichloride can be isolated from the reaction mixture and can be used in purified form for the reaction with ammonia.

According to the invention, the starting materials are mixed in a back-mixing-free manner. In the process according to the invention, "mixing in a back-mixing-free manner" means that the starting materials are mixed with each other sufficiently rapidly so that, during the mixing process, no substantial reaction of the starting materials, or none at all, takes place. In general, less than 5 (mol/mol) % of the amido-dichloride is reacted. It is also possible for more than 20 (mol/mol) % of the amido-dichloride to react. But preferably no more than 10 (mol/mol) %.

The concentration of the amido-dichloride during the mixing process in the mixing device is usually, when the operation is performed as intended, at all times below 0.5 (mol/mol) % of the reaction mixture, based on the volume of the reaction mixture, preferably below 0.3 (mol/mol) %, based on the volume of the reaction mixture. In an especially preferred embodiment, the concentration of the amido-dichloride in the mixing device during the mixing process is at all times below 0.2 (mol/mol) %, based on the volume of the reaction mixture.

Operation as intended means, in the present context, the continuous operation with the exclusion of the starting-up and shutting-down of the operation.

The mixing time of the starting materials is preferably very short and is in the second range. In general, the mixing time is less than five seconds, preferably less than two seconds. In an especially preferred embodiment, the mixing time of the starting materials in the mixing device is less than one second.

By mixing time there is meant, in the present process, the time span which elapses from the introduction of the starting materials into the mixing device until the mixing process has ended. The mixing time here is as defined in the publication VTB Verfahrenstechnische Berechungsmethoden [Process-engineering calculation methods], part 4, Stoffvereinigung in fluiden Phasen [Combination of substances in fluid phases], page 84, section 3. A technical mixing quality of 95% is usual.

Mixing the amido-dichloride with liquid ammonia is usually performed in a mixing device. Mixing is preferably performed at a high shear rate, upstream of the reaction reactor. Depending on the mixing device used, the starting materials may be introduced in preferably liquid form, but also in gaseous form. In the process according to the invention, mixing device means any container or any device in which two or more substances mix with one another as the result of elements incorporated within the mixing device or as the result of the pulse which the starting materials receive when introduced, for example by a nozzle. Depending on the scale of the reaction batch, a variety of mixing devices may be employed. In the case of smallish laboratory scales, a person skilled in the art can employ mixing devices known per se, such as stirrers, such as, for example, propeller stirrers, disk stirrers, crossbar stirrers or inclined-blade stirrers with a high speed. In a preferred embodiment, inclined-blade stirrers with a speed of from 500 to 1000 rpm, preferably 600 to 900 rpm, particularly preferably 750 to 850 rpm are used. The speed of an inclined-blade stirrer of, for example, 800 rpm is sufficient for achieving inventive short mixing times. On a large scale, the mixing device is, in a preferred embodiment, a nozzle, a rotor-stator mixer, a reaction mixing pump or a jet mixer equipped with nozzle. The mixing device is preferably a nozzle or a jet mixer equipped with nozzle. In an especially preferred embodiment, the mixing device is a nozzle. Preferred, but not limiting, embodiments are described in VTB Verfahrenstechnische Berechungsmethoden, part 4, Stoffvereinigung in fluiden Phasen, sections 3.5 and 3.6.

To cool the reaction mixture, one may employ ammonia in an excess, so that some of the ammonia evaporates after mixing (evaporative cooling).

Usually, amido-dichloride and ammonia are placed into the mixing device in a molar ratio of from 2 to 25 mol of ammonia per mole of amido-dichloride. Preferably, more than 2 mol of ammonia per mole of amido-dichloride are placed into the mixing device. More preferably, 16 or less than 16 mol, but more than 2 mol, of ammonia per mole of amido-dichloride are placed into the mixing device. Especially preferably, from 2 to 15, very especially preferably from 3 to 10, mol of ammonia per mole of amido-dichloride are placed into the mixing device. Particularly preferred is a molar ratio of from 4 to 6 mol of ammonia per mole of amido-dichloride.

In a preferred embodiment, the starting materials are cooled before mixing begins to such an extent that no substantial reaction takes place before the mixing time has ended. To this end, the starting materials are cooled to below 10° C., preferably to below 5° C., especially preferably to below 1° C. In an especially preferred embodiment, the starting materials are cooled to below 0° C.

After mixing in the mixing device in a back-mixing-free manner, the starting materials are generally reacted in a reactor. In a preferred embodiment, the reactor is a tube reactor or a loop-type bubble column. In an especially preferred embodiment, the reactor is a tube reactor. Since the reaction of amido-dichlorides and ammonia is highly exothermic, it is particularly preferred to employ a tube reactor which is a heat exchanger.

The temperature of the reaction in the tube reactor is maintained at temperatures which are conventional for this reaction. It is by preference from −30° C. to 50° C., preferably from −10° C. to 10° C., especially preferably −5° C. to 8° C.

The reaction discharge of the tube reactor is generally transferred into a device in which the product of interest is separated from the ammonia. Preferably, the device takes the form of a column at the bottom of which the product of interest is drawn off.

All process steps can be carried out without pressure or else under pressure. When carrying out the process steps under pressure, the superatmospheric pressure is preferably less than 50 bar, preferably less than 10 bar.

The reaction can be carried out batchwise or continuously.

The ammonia separated from the process can be recirculated into the process in a manner known to the skilled worker.

In a preferred embodiment, the above-described process is used to prepare N-alkylthiophosphoric triamides. In an especially preferred process, N-n-butylthiophosphoric triamide (NBPT) and N-propylthiophosphoric triamide or a mixture thereof is produced.

Thiophosphoric triamides, specifically N-n-butylthiophosphoric triamide (NBPT), are effective urease inhibitors which are employed in urea-based fertilizer compositions. Such urease inhibitors can improve the efficiency of urea fertilization since losses due to urease-catalyzed degradation of urea in the soil are reduced. (Trenkel, M. E., "Controlled-Release and Stabilized Fertilizers in Agriculture", IFA 1997, ISBN: 2-9506299-0-3).

For example, the thiophosphoric triamides prepared in accordance with the invention are employed as additive to urea-comprising mineral and/or organic-mineral fertilizers.

It is known that thiophosphoric triamides are hydrolyzed relatively readily to give the corresponding phosphoric triamides. In the presence of moisture, thiophosphoric triamides and their corresponding phosphoric triamides are, as a rule, present in the form of a mixture with each other. Within the scope of the present invention, the term "thiophosphoric triamide" therefore refers not only to the pure thiophosphoric triamides, but also to their mixtures with the corresponding phosphoric triamides.

The reaction according to the invention of thiophosphoric trichloride with at least one amine and ammonia in an inert solvent with the aid of at least one base which forms a hydrochloride salt with hydrogen chloride for the preparation of thiophosphoric triamides is preferably carried out in the following molar ratios:

In an advantageous embodiment, one mole of amine is employed approximately per mole of thiophosphoryl chloride. The amine is preferably used in a molar ratio of from 0.9 to 1.1 mol per mole of thiophosphoryl chloride, especially preferably from 0.95 to 1.05 mol of amine per mole of thiophosphoric trichloride.

The auxiliary base employed can be recovered readily, advantageously by neutralization with a stronger base. The base salt of the stronger base can be recovered by means of extraction or via phase separation with ammonia (U.S. Pat. No. 5,770,771).

The discharge of the reaction can freed from solvent, auxiliary base and any residual ammonia by distillation and can subsequently dried, for example in vacuo at temperatures less than 95° C., preferably less than 75° C., especially preferably less than 65° C. To dry the product further, it is also possible to employ a thin-film evaporator which is operated in vacuo at preferably approximately 90° C.

The invention is illustrated in greater detail in the use examples which follow; this, however, does not constitute a corresponding limitation.

EXAMPLES

The experiments, which were carried out in a batch reactor, were carried out with different mixing times, using 10 and 20 mol of $NH_3$/mole $PSCl_3$. The yields obtained in examples 1 and 2 according to the invention exceed those known from the prior art, for example those in the publication U.S. Pat. No. 5,770,771, which amounted to 92.4%.

The mixing time of the experiments was calculated using a method known to a person skilled in the art (Mischzeitcharakteristik [Mixing times characteristics], Stieβ, Mechanische Verfahrenstechnik [Mechanical process engineering], volume 1, p. 232 et seq.; Mischen und Rühren, Grundlagen und moderne Verfahren für die Praxis [Mixing and stirring, basics and modern processes for practice], Baden-Baden, 1998, p. 43-49) and Computational Fluid Dynamics (CFD) methods.

Example 1

| Starting materials: | | |
|---|---|---|
| 56.25 g | ethyl acetate | |
| 25.41 g | $PSCl_3$ | 0.15 mol |
| Reaction: | | |
| 18.75 g | ethyl acetate | |
| 23.64 g | tripropylamine (TPA) | 0.165 mol |
| 7.77 g | n-butylamine | 0.106 mol |
| 2.7 g | n-propylamine | 0.046 mol |
| 25.5 g | $NH_3$ | 1.5 mol |
| 20 g | ethyl acetate | |

Dichloride Synthesis:
56.25 g of ethyl acetate were placed into the reaction vessel together with 25.41 g of thiophosphoryl chloride. Then, the dichloride suspension was prepared by adding 23.64 g of tripropylamine, 7.77 g of n-butylamine and 2.7 g of n-propylamine.
Synthesis of Thiophosphoric Triamide:
A pressure apparatus which had been cooled to −20 degrees was charged with 25.5 g of liquid ammonia under a pressure of 4 bar. Using a pump, 5 g of ethyl acetate (EA) were introduced therein. Using a rotating plunger pump, 132.6 g of dichloride suspension were added with stirring (mixing device: inclined-blade stirrer, n=800 min-1), during which process the temperature in the reaction vessel did not climb beyond 0° C. due to cooling. After the dichloride suspension had been transferred into the reaction vessel, a further 15 g of EA were pumped into the reaction vessel.
The mixing time of the starting materials in this batch using this mixing device was 3 seconds.

The yield of the reaction was determined by means of HPLC and amounted to 68.3% of NBPT and 25.4% of NPPT, a total of 93.7% of product of interest.

Example 2

| Starting materials: | | |
|---|---|---|
| 56.25 g | ethyl acetate | |
| 25.41 g | $PSCl_3$ | 0.15 mol |
| Reaction: | | |
| 18.75 g | ethyl acetate | |
| 23.64 g | tripropylamine (TPA) | 0.165 mol |
| 7.77 g | n-butylamine | 0.106 mol |
| 2.7 g | n-propylamine | 0.046 mol |
| 51.1 g | $NH_3$ | 3.0 mol |
| 20 g | ethyl acetate | |

Dichloride Synthesis:
56.25 g of ethyl acetate were placed into the reaction vessel together with 25.41 g of thiophosphoryl chloride. Then, the dichloride suspension was prepared by adding 23.64 g of tripropylamine, 7.77 g of n-butylamine and 2.7 g of n-propylamine.
Synthesis of Thiophosphoric Triamide:
A pressure apparatus was cooled to −20° C. This pressure apparatus was charged, via a balance, with 51.1 g of ammonia, the pressure amounted to 4 bar. A connected pump was started up with 5 g of EA. Using a rotating plunger pump, 133.5 g of the dichloride suspension were added with stirring (mixing device: inclined-blade stirrer, n=800 min-1). The temperature in the reaction vessel did not climb above 0° C. as the result of cooling. After all of the dichloride suspension had been added, a further 15 g of EA were added to the mixture. The adding time amounted to 43 min, the temperature in the reaction vessel was between −10.3 and 0° C.
The mixing time of the starting materials in this batch using this mixing device was 3 seconds.
The yield of the reaction was determined by means of HPLC and amounted to 70.5% of NBPT and 25.9% of NPPT, a total of 96.4% of product of interest.

Example 3

Comparative Example

| Starting materials: Initially introduced mixture: | | |
|---|---|---|
| 56.25 g | ethyl acetate | |
| 25.41 g | $PSCl_3$ | 0.15 mol |
| Reaction: | | |
| 18.75 g | ethyl acetate | |
| 23.64 g | tripropylamine (TPA) | 0.165 mol |
| 7.77 g | n-butylamine | 0.106 mol |
| 2.7 g | n-propylamine | 0.046 mol |
| 25.5 g | $NH_3$ | 1.5 mol |
| 20 g | ethyl acetate | |

Dichloride Synthesis:
56.25 g of ethyl acetate were placed into the reaction vessel together with 25.41 g of thiophosphoryl chloride. The dichloride suspension was prepared by adding 23.64 g of tripropylamine, 7.77 g of n-butylamine and 2.7 g of n-propylamine.

Synthesis of Thiophosphoric Triamide:

A pressure apparatus was cooled to −20° C. This pressure apparatus was charged, via a balance, with 25.5 g of ammonia, the pressure amounted to 4 bar. A connected pump was started up with 5 g of EA. Using a rotating plunger pump, 6 g of the dichloride suspension were added with stirring (mixing device: inclined-blade stirrer, n=100 min-1). The temperature in the reaction vessel did not climb above 0° C. as the result of cooling. After all of the dichloride suspension had been added, a further 15 g of EA were added to the mixture.

The mixing time of the starting materials in this batch using this mixing device was 35 seconds.

The yield of the reaction was determined by means of HPLC and amounted to 60.6% of NBPT and 24.5% of NPPT, a total of 85.1% of product of interest.

Example 4

275.14 kg/h of a mixture (0° C.) of dichloride (63.0 kg/h), tripropylamine (4.4 kg/h), tripropylamine hydrochloride (55 kg/h) and ethyl acetate (152.43 kg/h) are mixed with each other together with 107.3 kg/h of liquid ammonia (0° C.) in a mixing nozzle with a mixing time of <0.1 s. The mixing is performed at a high shear rate and a sharp drop in pressure.

The mixing product is conveyed to a pressurized tube reactor. The product mixture is processed by distillation and under mild thermal conditions at low pressures. At the exit of the reaction stage, 49.07 kg/h of thiophosphoric triamide (NBPT) are formed.

The invention claimed is:

1. A process for the preparation of triamides from ammonia and amido-dichlorides, the process comprising:
    mixing starting materials of ammonia and amido-dichlorides in a mixing device to form a reaction mixture;
    reacting the reaction mixture in a back-mixing-free manner; and
    maintaining the concentration of the amido-dichlorides in the mixing device below 0.2 (mol/mol) % of the reaction mixture based on the volume of the reaction mixture.

2. The process according to claim 1, wherein a mixing time of the starting materials is less than one second.

3. The process according to claims 1, wherein mixing the starting materials is performed by one of a nozzle, a rotor-stator mixer, a reaction mixing pump, or a nozzle-equipped jet mixer.

4. The process according to claim 3, wherein the reaction mixture is transferred into a tube reactor.

5. The process according to claim 4, wherein the tube reactor is a heat exchanger.

6. The process according to claim 4, wherein the starting materials are cooled to below 0° C. before being mixed.

7. The process according to claim 4, wherein a heat of reaction in the tube reactor is dissipated by evaporating ammonia.

8. The process according to claim 4, wherein a reaction discharge from the tube reactor is transferred into a column.

9. The process according to claim 8, wherein a triamide is drawn off at a bottom of the column.

10. The process according to claim 9, wherein the triamide is N-alkylthiophosphoric triamide.

* * * * *